us005433894A

United States Patent [19]

Massaro et al.

[11] Patent Number: 5,433,894
[45] Date of Patent: * Jul. 18, 1995

[54] COMPOSITIONS COMPRISING FATTY ACID ESTERS OF ALKOXYLATED ISETHIONIC ACID & PROCESS FOR MAKING

[75] Inventors: Michael Massaro, Ridgefield Park; George Grudey, Hewitt; Leonora Ilardi, Englewood, all of N.J.

[73] Assignee: Lever Brothers Company, Division of Conopco, Inc., New York, N.Y.

[*] Notice: The portion of the term of this patent subsequent to Feb. 28, 2012 has been disclaimed.

[21] Appl. No.: 190,628

[22] Filed: Feb. 2, 1994

Related U.S. Application Data

[63] Continuation-in-part of Ser. No. 796,748, Nov. 25, 1991, abandoned.

[51] Int. Cl.$^6$ .......................... C11D 1/12; C11D 1/755
[52] U.S. Cl. .................................... 252/549; 252/554; 252/DIG. 1; 252/DIG. 4; 252/DIG. 16
[58] Field of Search ............... 252/549, 554, DIG. 1, 252/DIG. 14, DIG. 16

[56] References Cited

U.S. PATENT DOCUMENTS

| 3,029,264 | 4/1962 | Alphen et al. | 260/400 |
| 5,232,633 | 8/1993 | Ilardi et al. | 252/554 |
| 5,393,466 | 2/1995 | Ilardi et al. | 252/549 |

FOREIGN PATENT DOCUMENTS 974124  11/1964  United Kingdom .

Primary Examiner—Paul Lieberman
Assistant Examiner—Patricia Hailey
Attorney, Agent, or Firm—Ronald A. Koatz

[57] ABSTRACT

The present invention provides novel fatty acid esters of alkoxylated isethionic acid and compositions comprising these compounds. Using the alkoxylated isethionates, stable, concentrated (greater 10% total active) solutions can be prepared (when isethionate is primary surfactant) which would not have been possible to prepare using nonalkoxylated isethionate.

10 Claims, No Drawings

COMPOSITIONS COMPRISING FATTY ACID ESTERS OF ALKOXYLATED ISETHIONIC ACID & PROCESS FOR MAKING

RELATED APPLICATIONS

The present application is a continuation-in-part of U.S. Ser. No. 07/796,748, filed Nov. 25, 1991 now abandoned.

BACKGROUND OF THE INVENTION

1. Field of the Invention

The present invention relates to fatty acid esters of alkoxylated isethionic acid and specifically to compositions comprising the fatty acid esters.

2. Prior Art

The use of alkoxylated isethionates having the formula

R-(OCH$_2$ CH$_2$)$_n$SO$_3$$^-$Na$^+$ is known in the art, for example, from U.S. Pat. No. 3,823,185 to Schlossman.

The use of fatty acid esters of isethionate, e.g., sodium cocoyl isethionate having the formula $$CH_3(CH_2)_{10-12}\overset{O}{\overset{\|}{C}}-OCH_2CH_2SO_3^-Na^+$$

is also known in the art (see for example, Rys et al., U.S. Pat. No. 4,954,282).

U.S. Pat. No. 3,029,264 to Alphen et al. teach compounds of formula RCOOR'SO$_3$M. To the extent R' may be a dialkylene ether radical as disclosed at column 2, line 34, the reference, at least in theory, discloses fatty acid esters of a monoethoxylated isethionate. Although it is stated at column 3, lines 21-23, that products of the invention can be used to make detergent tablets, it is clear from the reference that none of the compounds made were ethoxylated isethionates (see Examples 1-9) and it is further clear that none of the compounds were formulated in any event (there are no formulation examples). Thus, the reference clearly fails to recognize that ethoxylated isethionates can be made or that, if made, they might have any advantages, i.e, formulation advantages, over their non-ethoxylated counterparts.

British Patent No. 974,124 (Shell) teaches compounds at column 1, line 3, where, if x is zero and n is 2, the compound may be diethoxylated. However, the R group is a secondary or tertiary carbon CR$_1$R$_2$R$_3$ which differs from the compounds of the invention. Further, there is no recognition of the specific formulation advantages of the diethoxy compound.

SUMMARY OF THE INVENTION

Surprisingly, it has now been found that fatty acid esters of alkoxylated isethionates can be much more readily formulated than nonalkoxylated isethionates. That is, alkoxylated isethionates are readily soluble in water when used as primary active (active comprises 50-100% of total active, wherein total actives comprise at least 10% by weight of the water solution) while nonalkoxylated isethionates when used as primary surfactants (i.e., greater than 50% of total active) are generally sparingly soluble in water when total actives comprise at least 10% by wt. of the water solution. Indeed alkoxylated isethionates are so much more soluble that they can be formulated even in the absence of coactives (although this is not preferred) while, if coactives are absent, nonalkoxylated isethionates cannot be formulated at all. Further, in the absence of coactive, the alkoxylated isethionate can comprise as little as 3% by wt. By contrast, even with coactive, where the primary surfactant is nonalkoxylated, the actives cannot comprise more than 10% of system while remaining soluble.

In addition, it has been found that the alkoxylated isethionates are superior to fatty acid esters of identical non-alkoxylated isethionates in mildness (as shown both by in vitro zein solubilization tests and confirmed by in vivo occlusive patch tests). Mildness of the alkoxylated isethionate has been further shown in clinical tests.

Also, the alkoxylated isethionates perform as well or better than nonethoxylated equivalents (as measured by Ross-Miles foam heights and/or with lather volume tests). These compounds are also much more calcium tolerant.

Specifically, the present invention relates to compositions comprising alkoxylated isethionate surfactants having the general formula:

$$R-\overset{O}{\overset{\|}{C}}-O-\overset{R'}{\overset{|}{CH}}-CH_2-(O-\overset{R''}{\overset{|}{CH}}-CH_2)_m-SO_3^-M^+$$

wherein R is a straight chain alkyl group having 8 to 18 carbons, m is an integer from 1-4, R' and R" are hydrogen or an alkyl group having from 1-4 carbons, and M$^+$ is a monovalent cation such as, for example, sodium, potassium or ammonium.

As indicated above, such compounds are far more soluble than their nonalkoxylated counterparts and can be formulated even in the absence of cosurfactants. Also, they can be readily formulated at levels greater than 10% total active when used as primary active. When used in non-liquid compositions, they may comprise 30-70% by wt. of the compositions and even in liquid compositions, may comprise up to 30% by wt. of the composition. In other words, much more concentrated solutions can be made compared to when the nonalkoxylated counterpart is used. Finally, the compounds have been found to be superior to similar compounds where m equals 0 (i.e., non-alkoxylated compounds) in both mildness and performance.

As indicated in more detail below, the surfactant compound used in the compositions of the invention may be prepared by reacting a sulfoalkoxy alcohol and a fatty acid by direct esterification. Since sulfoalkoxy alcohol may be formed by the reaction of sodium isethionate and a mixture of alkylene oxide groups, the resulting sulfoalkoxy alcohol can contain a mixture of alkoxylated groups (e.g., the molecule might contain both ethoxy and propoxy groups). Stated differently, if m>1 (i.e., 2-4), the Y group may differ from one alkoxylate group to another.

Further, since the sulfoalkoxy alcohol obtained is then reacted with fatty acids which typically comprise a mixture of R groups, the alkoxylated isethionate produced comprise a mixture of R groups as well (ranging from C$_8$ to C$_{18}$). The R group is a straight chain alkyl group.

As indicated above, the invention relates to the use of these surfactant compounds and to compositions containing these compounds. Among the compositions in which the surfactant may be used include both heavy and light-duty liquid detergent compositions, detergent bar compositions and personal product compositions (e.g., shampoos or facial cleansers or foam baths).

In a specific embodiment of the invention, the composition formed is a stable, concentrated (i.e., greater than 10% total active), homogeneous solution or dispersion which would have been extremely difficult to form (i.e., the solution would have precipitated) if a nonalkoxylated compound had been used. In the absence of cosurfactants, the nonalkoxylated compound will definitely precipitate.

In a different aspect of the invention, the invention provides a process for forming a stable, concentrated, homogeneous solution or dispersion (i.e., a solution or dispersion which does not phase separate or precipitate at room temperature over a 1 month period), which process comprises adding to a composition comprising (1) an alkoxylated isethionate (2) water and (3) minors (e.g. perfume, preservatives, electrolyte, opacifiers and humectants) and an amount between 0 and 50% by wt. (of surfactant system) of a cosurfactant selected from the group consisting of nonionic, anionic, cationic and zwitterionic surfactants. Since the alkoxylated isethionates are so much more soluble than nonalkoxylated counterparts, they are much more readily formulated over a broad range of active to coactive ratio and may be formulated without coactive at all. By contrast, when nonalkoxylated isethionate is used, the formulation of a stable composition can only be achieved by extreme delicate balancing of coactives (which enhance solubility) and fatty acids (which diminish solubility). Formulation becomes extremely difficult and the compositions, even if stably formed, are constantly in danger of phase separation or precipitation. In addition, when nonalkoxylated isethionates are used, at least some cosurfactant is required since the compositions cannot be stably formulated completely in their absence. Concentrated compositions with greater than 10% by wt. total active cannot be formed at all when alkyl nonalkoxylated isethionates comprise the primary active.

The process of the invention involves steady mixing (e.g., high shear mixing is preferred although this is not required) at a temperature of from about 40°-80° C., preferably 50°-70° C. and then allowing the composition to cool.

For reasons noted above, the compounds used in the compositions of the invention are mixtures of alkoxylated isethionates, wherein each alkoxylated isethionate might contain a mixture of alkoxylated groups and wherein there is a mixture of straight chain alkyl groups among the various alkoxylated isethionates.

DETAILED DESCRIPTION OF THE INVENTION

The present invention provides compositions comprising alkoxylated isethionate surfactants having the formula:

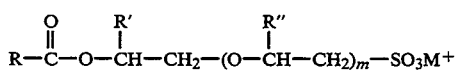

wherein R is a straight chain alkyl group having 8 to 18 carbons, m is an integer from 1-4, R' and R" are hydrogen or an alkyl group having from 1-4 carbons, and M$^+$ is a monovalent cation such as, for example, sodium, potassium or ammonium.

When these surfactant molecules were compared to molecules identical except that they were not alkoxylated, significant improvements in both mildness and performance were observed. The compounds are also much more calcium tolerant.

In addition, as discussed above, the alkoxylated surfactants are more water soluble and much easier to formulate over a broad range of primary active (i.e., alkoxylated isethionate to coactive ratio and may even be formulated in the absence of coactive altogether). More specifically, when alkoxylated isethionate is used as primary active of an active system (i.e., ratio of isethionate:coactive is greater than 1:1), it is readily possible to formulate concentrated compositions (having greater than 10% total active) while this is not possible when using a nonalkoxylated counterpad as the primary active.

Preparation

The alkoxylated molecules of the invention may be prepared in several ways. In one embodiment of the invention, the molecules may be prepared by first preparing an alkoxylated isethionate via the sulfonation of a corresponding chloroalkoxy lower alcohol (e.g., 2-(2-chloroethoxy)ethanol) and then treating the sulfoalkoxy lower alcohol (e.g., 2-(2-sulfoethoxy)ethanol) so formed with an alkoyl chloride wherein the alkoyl group has 8 to 18 carbons (e.g., lauroyl chloride) to form the described ester. An example of this process in set forth below:

An example of this process is set forth below:

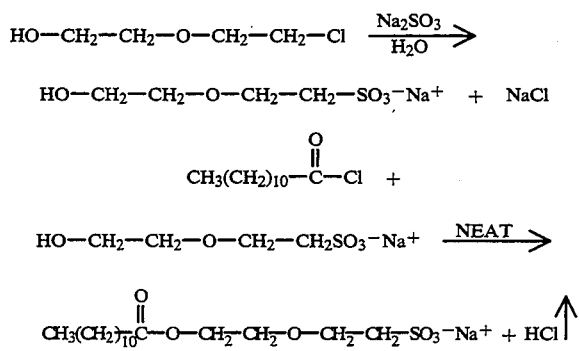

The reaction is described in greater detail in the examples below.

In another embodiment, the sulfoalkoxyalcohol may be produced by a reaction of alkylene oxide and sodium isethionate and a resulting reaction product then reacted with a fatty acid via acid catalysis to form the desired ester. An example of this direct esterification reaction is set forth below:

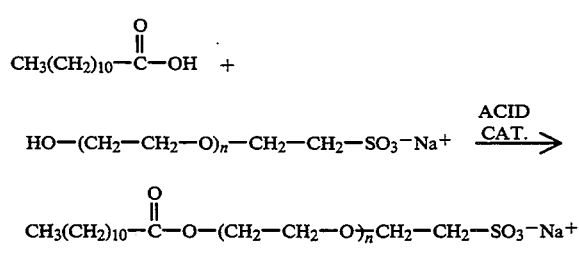

wherein n = 1-4 wherein n = 1-4

As indicated above, since the sulfoalkoxyalcohol can be formed from a mixture of alkylene oxides, the resulting alcohol may comprise a mixture of alkoxy groups (e.g., might contain both ethoxy and propoxy groups). As also indicated above, the fatty acid is generally a mixture of fatty acids of varying chain lengths and the reaction product will accordingly generally be a mixture of alkoxylated isethionates with a distribution of various alkyl groups.

Compositions

The alkoxylated isethionate surfactant compounds of the invention may be used in any cleaning or cleansing composition as may be known to those skilled in the art. For example, the components may be used in various personal washing compositions such as detergent bars, hand or body cleansers, shampoos as well as other compositions where mild surfactants might be desired (e.g., light duty liquid dishwashing compositions). The surfactants might also be used in a general cleaning or cleansing compositions.

The compounds of the invention are especially useful for liquid compositions for personal washing since it has not previously been possible to formulate stable, concentrated (i.e., greater than 10% by weight total actives) liquid compositions containing both isethionate and a coactive wherein the ratio of isethionate to coactive is 1:1 or greater, preferably above 1.5:1, more preferably above 2:1, most preferably 2:1 to 100:1. The isethionate of the invention may even be formulated in the absence of coactive altogether. More specifically, while not wishing to be bound by theory, it is believed that the alkoxylated isethionates are more water soluble and therefore greater amounts can be mixed with coactive in stable liquid personal wash compositions. Thus, for example, when using nonethoxylated isethionate to coactive at these ratios, no more than 10% total active has been successfully incorporated into the composition. By contrast, with alkoxylated isethionate, solutions having from 10% to 70% by weight total active can be prepared depending on the length and distribution of the alkyl chain on the surfactant. In liquid formulations, the upper limit of total actives is about 30% by wt. In non-liquid formulations, the total actives is preferably used in an amount from 30–60% by wt.

To the extent that the surfactants may be used in any cleaning or cleansing composition known to those skilled in the art, it will be understood by those skilled in the art that the surfactants may be used in combination with one or more cosurfactants in binary active compositions, ternary active compositions, etc.

In addition, the compositions of the invention comprising the alkoxylated isethionate provide mildness advantages, foam better and are more calcium tolerant than compositions comprising the nonethoxylated counterpart.

These examples are not intended to be exhaustive of the compositions in which such mild surfactants might be used and other compositions in which such mildness might be desirable would be apparent to those skilled in the art.

As noted, the compositions of the invention comprise 10% to 70% by weight of a surfactant active system (preferably 10–30% by wt. when the surfactant system is used in liquid compositions and 30–60% when used in non-liquid formulations) wherein the compound or mixture of the compounds of the invention (i.e., the alkoxylated isethionate of the invention) is the primary surfactant of the active system, i.e., comprises 50% to 100% of the active system, and a cosurfactant comprises less than 50% of the active system. The cosurfactant comprises 0–20% by weight of the total composition (as long as it is less than 50% of the active system) and is selected from the group consisting of anionic, nonionic, cationic, ampholytic and zwitteronic surfactant and mixtures thereof. The alkoxylated isethionate comprises 5% to 70% by weight of the total composition, preferably 10 to 30% by weight for liquids and 30%–60% for non-liquid compositions.

Examples of the many co-surfactants which may be used are set forth in U.S. Pat. No. 5,071,586 to Kaiserman et al., hereby incorporated by reference into the present specification.

In a second embodiment of the invention, the invention relates to a process for preparing high lathering, mild and stable liquid cleansing compositions which process comprises utilizing alkoxylated fatty acid isethionate rather than the nonalkoxylated isethionate. Specifically, the invention is a process for making such high lathering, mild and stable liquid cleansing compositions which process comprises mixing 5 to 30% alkoxylated isethionates having the formula defined above with 0–20%, preferably 1 to 15% by weight, more preferably 5% to 10% by weight of a cosurfactant or cosurfactants selected from the group consisting of anionic, nonionic, cationic, ampholytic and zwitterionic surfactants or mixtures thereof.

The process comprises mixing together the components of the system at a temperature of from about 40° C. to 80° C., preferably 50°–70° C., most preferably 60° C. 30 minutes to about 5 hours and then allowing to cool.

Unless stated otherwise, all percentages noted in the specification and examples are percentages by weight.

The present invention is further illustrated by the following examples which are not intended to be limiting in any way.

EXAMPLE 1

Preparation of Sodium Lauroyl Monoethoxy Isethionate

Preparation of Sodium 2-(2-Sulfoethoxy)ethanol

Into a three-neck, 250 ml round-bottomed flask equipped with water condenser, magnetic stir bar, oil bath, and temperature-controlled hot plate stirrer was placed 150 mL distilled deionized water and 50.2 g (0.398 moles) $Na_2SO_3$. This mixture was stirred till all the inorganic salt was dissolved. To this was added 50.0 g (0.398 moles) of freshly distilled 2-(2-Chloroethoxy)ethanol. Upon addition, a two phase reaction mixture was noted due to the insolubility of the starting organic in water. The mixture was heated to reflux for 24 hours. After this time, a clear,colorless, one phase reaction mixture was noted. Approximately 80% of the water was removed under reduced pressure using a rotary evaporator leaving a thick, colorless, opaque gel. This was poured into two crystallizing dishes and dried in a vacuum oven at 45° C. for 48 hours. After this time, 524 g of a white, brittle solid was recovered from one dish. It was analyzed to contain 23.7% NaCl. The other dish contained 245 g of a white solid analyzed to contain 10.2% NaCl. The total weight of product recovered was 620 g which is a 94.3% yield. The material can be recrystallized from ethanol and water to remove the sodium chloride and purify the material. 1 H NMR (200

MHz, D₂0, TMS): Δ3.2 (2H,t); Δ3.62–3.75 (4H,m); Δ3.9 (2H, t).

Preparation of Sodium lauroyl Monethoxy Isethionate from Sodium 2-(2-sulfoethoxy)ethanol Into a 100 mL three-neck round-bottomed flask equipped with mechanical stirrer, oil bath with temperature controlled hot plate, inlet tube connected to a nitrogen source, and an outlet tube connected to a base (NaOH soln) trap, was placed 23.49 g (0.122 moles) of the previously prepared sodium 2-(2-Sulfoethoxy)ethanol and 26.80 g (0.123 moles) of distilled lauroyl chloride. The mixture was stirred and heated to 85° C. resulting in a white, viscous homogenous liquid. IR of the reaction after 30 min. showed completed condensation by the absence of the carbonyl stretch at 1800 cm⁻ for the acid chloride and the appearance of the product ester carbonyl at 1740 cm⁻¹. The reaction was placed under vacuum using a diaphragm pump to remove the HCl produced in the reaction. The resulting solid was washed with acetone, filtered and dried in a vacuum oven. A yield of 39.4 g (86%) was obtained. The material was recrystallized from 175 mL ethanol/100 mL water producing fine, needle-like crystals; 27.3 g recovered. Hyamine analysis of this material showed approximately 100.0% activity. Lauric acid analysis: 0.60%. Water: 0.8%. 1H NMR (200 MHz, TMS, D₂0): Δ0.86 (3H, broad t); Δ1.0–1.7 (18H, m); Δ2.36 (2H, t); Δ3.73 (2H, broad t); Δ3.87 (2H, broad t).

EXAMPLE 2

Preparation of Sodium Lauroyl Diethoxy Isethionate

Preparation of Sodium 2-[2-(2-Sulfoethoxy)ethoxy]ethanol

Into a three-neck, 250 mL round-bottomed flask equipped with water condenser, magnetic stir bar, oil bath, and temperature controlled hot plate stirrer was placed 100 mL of distilled deionized water and 32.2 g (0.295 moles) Na₂SO₃; the mixture was stirred until all salt was dissolved. To this was added 45 g (0.266 moles) of freshly distilled 2-[2-(2-Chloroethoxy)ethoxy]ethanol and the mixture was heated to reflux. Upon addition, the starting chloroethanol appeared as a second phase floating on top of the water. After 6 hours, a clear colorless reaction mixture resulted. HPLC analysis of the reaction mixture indicated that no starting chloroethoxyethanol remained. The reaction was placed under reduced pressure to remove most of the water resulting in a clear, colorless gel. The mixture was dried thoroughly in a vacuum oven to remove all water. A standard silver nitrate titration was conducted to assay for the percentage of sodium chloride in this material. The material was used as is in the acid chloride preparation of the ethoxylated active. 1H NMR (200 MHz, D20, TMS), Δ3.2 (2H, t); Δ3.62–3.75 (8H,m); Δ3.9 (2H, t).

Preparation of Sodium Lauroyl Diethoxy Isethionate from Sodium 2-[2-(-sulfoethoxy) ethoxy]ethanol Acid Chloride Preparation Into a 250 mL three-neck, round-bottomed flask equipped with mechanical stirrer, oil bath with temperature controlled hot plate stirrer, inlet tube connected to a nitrogen source, and an outlet tube connected to a base (NaOH soln) trap, was placed 59.14 g (0.251 moles) of the previously prepared sodium 2-[2-(-Sulfoethoxy)ethoxy]ethanol and 57.4 g (0.262 moles) of freshly distilled lauroyl chloride. The mixture was stirred and heated to 65° C. The reaction mixture took on an opaque, white appearance. After 30 minutes, the condensation appeared complete by IR showing the disappearance of the acid chloride carbonyl and the appearance of the product carbonyl at 1740 cm⁻¹. The reaction mixture was placed under reduced pressure using a diaphragm pump to remove HCl that was generated in the reaction. The resulting light tan colored solid was dissolved in water and its pH was adjusted from 2 to 7 using a dilute NaHCO₃ solution and the water was removed by freeze drying. The solid obtained amounted to 114 g; hyamine titration of this mixture indicated an 87% yield based on the starting 2-[2-(2-Chloroethoxy)ethoxyl]ethanol. The material was recrystallized three times from ethanol/water. The analysis of the final product showed about 98% activity (Hyamine titration). 1H NMR (200 MNz, D20, TMS): Δ0.88 (3H, broad t); Δ1.0–1.7 (18H, m); Δ2.36 (2H,t); Δ3.20 (2H,t); Δ3.67–3.80 (6H, m); Δ3.88 (2H, t); Δ4.24 (2H, broad t).

EXAMPLE 3

Preparation of Sodium Lauroyl Diethoxy Isethionate via Direct Esterification

Into a glass reactor consisting of a ground glass 100 mL cylindrical bottom piece and a four-neck top piece which is fitted with a thermocouple, a mechanical stirrer, a teflon nitrogen-gas inlet tube and a water condenser was placed 71.9 g (0.359 moles) of lauric acid, 0.151 g of Zinc Oxide catalyst and an approximately 50% solution of previously prepared sodium 2-[2-(2-Sulfoethoxy)ethoxy] ethanol (62.54 g (0.265 moles) in water). Nitrogen sparging at 40 cc/min was started and the reaction mixture was stirred and heated. At 45° C. the fatty acid began to melt and at 110° C., water began to boil off and was collected along with a small amount of fatty acid. After the water was removed, the reaction was heated to 235° C. for 90 minutes. After this time, the heat was removed and the mixture was allowed to cool and solidify. IR analysis of the reaction mixture showed carbonyl stretches at 1740 cm⁻¹ and 1710 cm⁻¹ indicating the product and the starting acid respectively. Hyamine titration of the mixture indicated a 81% activity.

EXAMPLE 4

Various characteristics of mono or di-ethoxylated isethionates were compared to nonethoxylated isethionate and the results are set forth below:

| | ETHOXYLATED ISETHIONATES | | | | |
|---|---|---|---|---|---|
| Active | CMC (mM) | Krafft Pt. (°C.) | Foam Ht.* (mm) | % Zein Solub. | $Ca^{+2}$ Needed for Prec. (ppm) |
| Sodium Lauroyl | 6.2 | 24 | negligible | 55 | 51 |

-continued

ETHOXYLATED ISETHIONATES

| Active | CMC (mM) | Krafft Pt. (°C.) | Foam Ht.* (mm) | % Zein Solub. | $Ca^{+2}$ Needed for Prec. (ppm) |
| --- | --- | --- | --- | --- | --- |
| Isethionate Sodium Lauroyl Monoethoxy Isethionate | 4.3 | 24 | 165/159** | 42 | 2400 |
| Sodium Lauroyl Diethoxy Isethionate | 2.7 | <0 | 154/151 | 35 | >4000 |

*Measured as 1% aqueous solution of surfactant.
**Before slash equals initial foam level and after slash is level after 10 minutes.

Each of these characteristics, how they are quantified, and an explanation of the significance of these numbers is set forth in greater detail below.

1. Critical Micelle Concentration (CMC)

The CMC is defined as the concentration of a surfactant at which it begins to form micelles in solution. Specifically materials that contain both a hydrophobic group and a hydrophilic group (such as surfactants) will tend to distort the structure of the solvent (i.e., water) they are in and therefore increase the free energy of the system. They therefore concentrate at the surface, where, by orienting so that their hydrophobic groups are directed away from the solvent, the free energy of the solution is minimized. Another means of minimizing the free energy can be achieved by the aggregation of these surface-active clusters or micelles with their hydrophobic groups directed toward the interior of the cluster and their hydrophilic groups directed toward the solvent.

The value of the CMC is determined by surface tension measurements using the Wilhemy plate method. While not wishing to be bound by theory, it is believed that a low CMC is a measure of surface activity (i.e., lower CMC of one surfactant versus another indicates the surfactant with lower CMC is more surface active). In this regard, it is believed that lower CMC signifies that lesser amounts of a surfactant are required to provide the same surfactancy benefits as a surfactant with higher CMC.

As can be seen from the table above, both mono and di-ethoxylated have lower CMC values and are therefore believed to provide more effective surfactancy.

2. Krafft Points

The temperature at and above which surfactants begin to form micelles instead of precipitates is referred to as Kraft point (Tk) and at this temperature the solubility of an ionic surfactant becomes equal to its CMC.

Krafft point was measured by preparing a 1% dispersion of the surfactant in water. If the surfactant was soluble at room temperature, the solution was cooled to 0° C. When the surfactant did not precipitate out, its Krafft point was considered to be <0° C. If it precipitated out, the solution was slowly warmed with stirring in a water bath. The temperature at which the precipitate dissolved was determined to be the Krafft point.

If the Krafft point was above room temperature, the solution was first heated rapidly to dissolve all the surfactant. It was then cooled until precipitation occurred, and was then slowly warmed to determine the Kraft point described above.

While not wishing to be bound by theory, it is believed that lower Krafft points are indicative of a surfactant being more soluble in aqueous system. In addition, it is believed that surfactants with lower Krafft points are easier to formulate in multi-electrolyte systems because of their greater tolerance to salt.

From the table above, it can be seen that the monoethoxy material has the same Krafft point as the nonethoxy material. However, the diethoxy material has a much lower Krafft point indicating greater solubility and salt tolerance as discussed above.

3. Foam Height

Foam is an impodant attribute in many consumer products (e.g., consumer products). Foam is one of the dominant factors that determines the commercial value of products such as shampoo, soap, etc. Also, acceptability of many consumer products is closely related to the quality and texture of the foam they produce (psychological aspect).

Since most of the foaming data on surfactants is typically obtained by the Ross-Miles method (Ross, J. and Miles, G. D., Am. Soc. For Testing material Method D1173-53 Philadelphia, Pa. (1953); Oil & Soap (1958) 62:1260) the foaming ability of these surfactants was also acquired using this method.

In the Ross-Miles method, 200 mL of a solution of surfactant contained in a pipette of specified dimensions with a 2.9-mm-i.d. orifice is allowed to fall 90 cm onto 50 mL of the same solution contained in a cylindrical vessel maintained at a given temperature (often 60° C.) by means of a water jacket. The height of the foam produced in the cylindrical vessel is read immediately after all the solution has run out of the pipette (initial foam height) and then again after a given amount of time (generally, 5 min).

Using this method, the foam production(measured initially) and foam stability (the height after 10 minutes) are reported. All of the foaming was achieved at 45° C. in water with 120 ppm hardness. The foam height is represented in millimeters (mm).

As indicated in the table above, foam heights for the nonethoxylated isethionate are negligible while heights for the ethoxylated isethionates are quite high.

4. Zein Test

In vitro "Mildness" Test

Assessing Mildness

Many factors have been reported to have an influence on skin irritation such as removal of skin lipids, loss of naturally occurring hygroscopic materials in the stratum corneum, adsorption, protein denaturation, and epidermal lysosomal injury. although there are many hypotheses regarding skin irritation, it is generally believed that surfactants become irritants because they penetrate the stratum corneum which is a "barrier" and then react with the inner cells of the epidermis.

Traditionally, the study of percutaneous absorption has focused on measuring the diffusion of chemicals (e.g., surfactants through stratum corneum). Diffusion through an organ as complex as skin and its associated adnexal appendages is challenging to measure, much less to model. Another challenge of cutaneous metabolism is to assess the irritating potential, toxicity, and therapeutic potential of the penetrating compounds.

In vivo, the skin metabolism and percutaneous absorption are very difficult to measure. Finding adequate detection methods and setting up proper experiments are not easy tasks. In vitro studies however are used because of the simplicity of the experimental conditions.

We have obtained information on mildness potentials of the surfactant by carrying out in vitro tests which have been demonstrated to correlate well with in vivo tests.

In Vitro Zein Solubilization Test

Gotte (E. Gotte, Proc. Int. Cong. Surface Active Subs., 4th Brussels (1964), 3, 83–90) and Schwinger (M. J. Schwinger, Kolloid-Z.Z.Poly., (1969), 233, 898) have shown that an anionic surfactant's ability to solubilize zein, an insoluble maize protein, correlates well with surfactant irritation potential. Specifically, the lower the amount of zein protein dissolved, the milder a surfactant is. Conversely, the more zein dissolved, the more irritating the surfactant is.

In order to test irritancy potential, a 1% solution of surfactant (30 mls) was added to 1.5 g zein and stirred at room temperature for 1 hr. Residual zein was collected and dried to constant weight. Differences between starting and residual weight were used to calculate % zein dissolved.

As seen from the table above, the decrease in zein dissolved going from the nonethoxylated material to the diethoxy material indicates a decrease in irritation potential.

5. Calcium Sensitivity

The calcium ion stability of ethoxylated isethionates was measured by a modified Hart method (Witkes, et al., J. Ind. Eng. Chem., 29, 1234–1239 (1937)). The surfactant solution was titrated with a calcium ion solution. The endpoint was determined by visual observation of the cloudiness of the surfactant solution.

Many surfactants like fatty soap are known to chelate with calcium ion to form calcium salts which are usually insoluble in aqueous media. This will lead to the loss of their surfactant properties. Calcium "insensitive" surfactants have unique advantageous properties for many applications such as a formulation for a liquid cleanser. In the case of the ethoxylated isethionates, it was noticed that a large amount of calcium ion was added before precipitation was seen. For the ethoxylated isethionates, the precipitation limit was not reached even at levels well over an order of magnitude higher than the precipitation limit for the nonethoxylated isethionate.

As clearly seen from the table above, ethoxylated isethionates are much less sensitive to calcium than the nonethoxylated compound.

6. Summary

In summary, the table above shows:
(1) ethoxylated isethionates have lower CMC than nonethoxylated isethionate (lower CMC being associated with superior surfactancy);
(2) at least the diethoxy isethionate has lower Krafft point (providing better surfactant solubility and improved formulation flexibility);
(3) ethoxylated isethionates provide superior foaming;
(4) ethoxylated isethionates have greater mildness potential as indicated by the decrease in irritation potential observed when conducting in vitro zein tests; and
(5) ethoxylated isethionates are more calcium insensitive (i.e., will not precipitate as easily).

EXAMPLE 5

In Vivo Mildness Evaluation

Two toilet bar compositions containing fatty acid esters of ethoxylated isethionic acid and one toilet bar composition with a nonethoxylated counterpad were prepared and the compositions are set forth below:

| Component (% by Wt.) | Composition 1 | Composition 2 | Composition 3 |
|---|---|---|---|
| Sodium cocoyl isethionate | — | 24.89 | 49.78 |
| Sodium lauroyl diethoxy isethionate | 51.37 | 25.69 | — |
| Lauric acid | 21.6 | 10.8 | — |
| Stearic acid | — | 10.08 | 20.15 |
| Coconut fatty acid | — | 1.54 | 3.01 |
| Soap (Mixture of tallow and coconut) | 8.02 | 8.02 | 8.02 |
| Sodium stearate | 3.01 | 3.01 | 3.01 |
| Sodium alkyl benzene sulfonate | 2.01 | 2.01 | 2.01 |
| Sodium chloride | 8.34 | 4.3 | 0.35 |
| Sodium isethionate | — | 2.34 | 4.68 |
| Water | 5.01 | 5.21 | 5.21 |
| Miscellaneous | 0.64 | 2.11 | 3.78 |

Each of the two bars (containing an alkoxylated surfactant compound of the invention) and the comparative bar (with nonalkoxylated compound) were tested using a patch test which was used to assess the in vivo mildness of formulations. According to the patch test, up to six formulations can be tested at the same time on each subject using occluded patches which remain on the forearm for 24 hours. Test sites are evaluated at 6 and 24 hours following the removal of the patches for erythema. A 0–4 scale was used in which 0 is no response and 4 is severe erythema.

Results of the patch tests are shown below:

| | 6 hours | | 24 hours | |
|---|---|---|---|---|
| Composition | Mean Score | Std. Dev. | Mean Score | Std. Dev. |
| 1 | 0.273 | 0.47 | 0.091 | 0.3 |
| 2 | 0.273 | 0.47 | 0.091 | 0.3 |
| Comparative | 0.818 | 0.07 | 0.455 | 0.52 |

Using standard statistical measurements, "significance" (in terms of mildness) in test results ins defined by 95% confidence, or better (p value $<0.05$). More specifically, p value is defined as the probability that two numbers are different due to chance rather than that they are really different. The lower the p value, the less likely that they are equal due to chance and the more likely that they are different. Thus a p value of 0.05 indicates that there is a 5% chance the observed differences are random coincidence and a 95% chance that the difference is a real difference. In the compositions above, both formulations 1 and 2 had a value of 0.03 (i.e., significance was established).

These tests thus clearly show that both Formulation 1 containing sodium lauroyl diethoxy isethionate, and Formulation 2 containing a combination of sodium lauroyl diethoxy isethionate and sodium cocoyl isethionate were significantly milder (p=0.03 for both formulations relative to comparative) relative to comparative composition containing only sodium cocoyl isethionate.

These in vivo mildness results corroborate the indications of mildness suggested by the zein tests.

Example 6

Lather Volumes

| Component (% by Wt.) | Composition 3 | Composition 4 | Comparative |
| --- | --- | --- | --- |
| Sodium cocoyl diethoxy isethionate | 49.8 | 33.4 | — |
| Sodium stearoyl diethoxy isethionate | — | 16.4 | — |
| Sodium cocoyl isethionate | — | — | 49.8 |
| Sodium tallowate/cocoate | 8.0 | 8.0 | 8.0 |
| Sodium stearate | 3.0 | 3.0 | 3.0 |
| Sodium alkylbenzene sulfonate | 2.0 | 2.0 | 2.0 |
| Fatty acid | 24.0 | 22.1 | 23.2 |
| Sodium chloride | 5.72 | 8.55 | 0.35 |
| Sodium 2-[2-(2-sulfoethoxy) ethanol | 1.7 | 1.4 | — |
| Sodium isethionate | — | — | 4.7 |
| Titanium dioxide | 1.0 | 1.0 | 1.0 |
| Water, fragrance, preservatives | to 100% | to 100% | to 100% |

Objective Lather Volumes

This test involved rotating the toilet bar 15 half turns under running 95° F. water. The bar was then set aside and the resulting lather was worked by hand for 10 seconds. A measuring funnel was then placed over the hands and both were lowered into a sink filled with water to the 0 ml mark on the measuring funnel. When the hands were fully immersed, they were removed from beneath the funnel. The funnel was then lowered to the bottom of the sink and lather volume was measured.

| Bar | Lather Volume (mL) |
| --- | --- |
| 3 | 94 |
| 4 | 97 |
| Comparative | 98 |

All bars tested had excellent lather volumes. Bars 3 and 4 containing diethoxy isethionates lathers as well as a commercially available comparative bar containing non-ethoxylated isethionate.

EXAMPLE 7

Light Duty Liquid Containing Ethoxylated Isethionates

A composition containing the following ingredients may be prepared:

| Component | % By Weight |
| --- | --- |
| Ammonium alkyl benzene sulfonate | 19.0 |
| Sodium lauroyl/myristoyl diethoxy isethionate | 11.0 |
| Lauric/myristic monoethanolamide | 3.0 |
| Sodium xylene sulfonate | 5.0 |
| Preservative, fragrance, dye and water | to 100% |

EXAMPLE 8

Hand or Body Cleanser Containing Ethoxylated Isethionates

A composition containing the following ingredients was prepared:

| Component | % By Weight |
| --- | --- |
| Sodium lauroyl/myristoyl diethoxy isethionate | 13.0 |
| Coco amido propyl betaine | 4.5 |
| Carbopol 940* | 1.0 |
| Laponite (clay) | 0.05 |
| Lauric/myristic acid | 5.6 |
| Sodium chloride | 2.8 |
| Preservative, fragrance, dye and water | to 100% |

*About 1% cross-linked polyacrylic acid having a molecular weight of about 4 million

EXAMPLE 9

Formulation of Alkoxylated Isethionates vs. Nonethoxylated Counterparts

In order to show that the alkoxy isethionate compounds used in this invention could be formulated and to further show that the compositions made were stable even at high concentrates of total active (i.e., greater than 10% by wt. total active), in contrast to the counterpads using nonalkoxylated isethionate, applicants prepared two sets of liquids.

The first set contained lauroyl DEFI (directly esterified $C_{12}$ fatty acid isethionate) with one of these coactives and water. The coactives used were an amphoteric cocoamido propylbetaine, an anionic (lauryl ether sulfate) or a nonionic (alkyl polyglucose). The fourth solution of the first set contained only lauroyl DEFI, water and salt. A second set of solution was then prepared analogous to the first except lauroyl diethoxy DEFI was used in place of the first.

Each solution was prepared with about 20% total active level and the ratio of active/coactive was 3:1

Upon mixing, heating and cooling, all four examples containing lauroyl DEFI exhibited phase separation and precipitation of active. That is, use of lauroyl DEFI in this type of application (20% active; 3:1 ratio) is severely limited.

By contrast, all four samples containing lauroyl diethoxy DEFI were stable, homogeneous solutions or dispersions, with no formation of precipitate. The mixtures containing amphoteric, anionic NaCl or, to some extent APG resulted in viscous, liquid crystalline phases, all of which lathered well.

This example clearly shows that the alkoxylated isethionate is much more soluble and much more readily formulated than its nonalkoxylated counterpart.

EXAMPLE 10

In order to show that nonalkoxylated isethionate could not be successfully formulated (when used as primary active) with a cosurfactant at concentrations higher than 10% total active, applicants prepared mixtures of nonalkoxylated lauroyl DEFI ($C_{12}$ fatty acid directly esterified isethionate esters) and APG (alkyl-poyglucoside), LES (lauryl ether sulfate) and cocoamidopropylbetaine. Each mixture was titrated with water until a stable mixture (no phase separation) occurred and the following results were observed:

| Mixture | % Active for Stable Solution/Dispersion |
|---|---|
| DEFI & APG (1:1) | 2% |
| DEFI & LES (1:1) | 2% |
| DEFI & CAPB (1:1) | 5% |

From the above, it can be clearly seen that stable mixtures cannot be found when level of total actives are too high. By contrast, when alkoxylated isethionate is used (as seen from Example 9, for example), active levels of 20% are readily reached.

We claim:

1. A cleaning or cleansing composition comprising:
   (1) 10% to 70% by wt. of a surfactant active composition, wherein said surfactant active composition comprises:
   (a) about 5% to about 70% by weight of a compound or mixture of compounds having the formula:

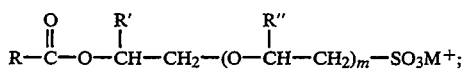

$$R-\overset{O}{\underset{\|}{C}}-O-CH-CH_2-(O-\overset{R''}{\underset{|}{CH}}-CH_2)_m-SO_3M^+;$$

(with R' on the first CH)

wherein R is a straight chain alkyl group having 8 to 18 carbons, m is greater than 1, R' and R" are hydrogen or an alkyl group having 1–4 carbons and $M^+$ is a monovalent cation; and (b) 1% to 15% by weight of a cosurfactant selected from the group consisting of anionic, nonionic, cationic, ampholytic and zwitterionic surfactants or mixtures thereof; wherein component (a) comprises 50 to 100% of total surfactant in said surfactant active composition.

2. A composition according to claim 1 wherein, in the compound of (a), the monovalent cation is selected from the group consisting of sodium, potassium and ammonium.

3. A composition according to claim 1 wherein, in the compound of (a) the R group on each compound within said mixture of compounds is a straight chain alkyl group having 8 to 18 carbons.

4. A composition according to claim 1, which is a non-liquid toilet bar composition and wherein the surfactant active composition comprises 30–60% by weight of the composition.

5. A composition according to claim 1, wherein the composition is a hand dishwashing composition.

6. A composition according to claim 1, wherein the composition is a facial cleanser composition.

7. A composition according to claim 1, wherein components (a) and (b) are used in combination with other cosurfactants.

8. A liquid cleaning composition comprising:
   (1) 10 to 30% by wt. of the surfactant active system of claim 1;
   (2) 2 to 10% by wt. electrolyte; and
   (3) 0 to 10% by wt. fatty acid.

9. A composition according to claim 8, wherein component (b) of the surfactant active system is cocoamidopropyl betaine, the electrolyte is NaCl and the fatty acid is $C_{10}$ to $C_{18}$ fatty acid or mixture of such fatty acids.

10. A process for making a stable, liquid cleaning composition which process comprises mixing 5% to 30% by wt. alkoxylated isethionate according to claim 1; 1 to 15% by weight coactive, wherein said coactive is selected from the group consisting of nonionic, anionic, cationic, amphoteric and zwitterionic surfactants; and water.

* * * * *

UNITED STATES PATENT AND TRADEMARK OFFICE
Certificate

Patent No. 5,433,894                                            Patented: July 18, 1995

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Michael Massaro, Congers, NY; George Grudev, Hewitt, NJ; Leonora Ilardi, Englewood, NJ; and Kennard Daniels, Madison, NJ.

Signed and Sealed this Eighth Day of June, 1999.

PAUL LIEBERMAN, *SPE*
Art Unit 1105